(12) United States Patent
Cranford et al.

(10) Patent No.: US 10,206,901 B2
(45) Date of Patent: Feb. 19, 2019

(54) METHOD AND COMPOSITION FOR ACUTE TREATMENT OF SEIZURES

(71) Applicant: JC Pharma, Inc., Boulder, CO (US)

(72) Inventors: Jason Allen Cranford, Denver, CO (US); Donald Channing Cooper, Boulder, CO (US)

(73) Assignee: JC Pharma, Inc., Boulder, CO (US)

( * ) Notice: Subject to any disclaimer, the term of this patent is extended or adjusted under 35 U.S.C. 154(b) by 0 days.

(21) Appl. No.: 15/710,204

(22) Filed: Sep. 20, 2017

(65) Prior Publication Data

US 2018/0078524 A1 Mar. 22, 2018

Related U.S. Application Data

(60) Provisional application No. 62/502,884, filed on May 8, 2017, provisional application No. 62/397,666, filed on Sep. 21, 2016.

(51) Int. Cl.
| | |
|---|---|
| *A01N 43/16* | (2006.01) |
| *A61K 31/35* | (2006.01) |
| *A61K 31/352* | (2006.01) |
| *A61K 9/00* | (2006.01) |
| *A61K 31/045* | (2006.01) |

(52) U.S. Cl.
CPC .......... *A61K 31/352* (2013.01); *A61K 9/0043* (2013.01); *A61K 31/045* (2013.01)

(58) Field of Classification Search
None
See application file for complete search history.

(56) References Cited

U.S. PATENT DOCUMENTS

| | | |
|---|---|---|
| 2002/0035068 A1 | 3/2002 | Kammen |
| 2012/0295936 A1 | 11/2012 | Donello et al. |
| 2014/0128379 A1 | 5/2014 | Bergenhem et al. |
| 2014/0243405 A1* | 8/2014 | Whalley ............ A61K 31/05 514/456 |
| 2015/0313868 A1* | 11/2015 | Morgan ............ A61K 31/352 514/221 |
| 2016/0158195 A1 | 6/2016 | Stroh |

FOREIGN PATENT DOCUMENTS

WO 2016059404 A1 4/2016

OTHER PUBLICATIONS

Schachter et al., "What Happens During a Seizure," https://www.epilepsy.com/learn/about-epilepsy-basics/what-happens-during-seizure, Mar. 19, 2014.*
PCT Notification of Transmittal of the International Search Report and the Written Opinion of the International Search Authority, or the Declaration dated Nov. 13, 2017 in connection with PCT International Patent Application No. PCT/US2017/52463, 10 pages.

* cited by examiner

*Primary Examiner* — Jared Barsky

(57) ABSTRACT

A nasal spray composition and method for treating convulsive seizures, including epileptic seizures, and also autism behavioral events. In embodiments, the nasal spray composition contains delta-9-tetrahydrocannabinol and, optionally, terpenes such as linalool.

2 Claims, 1 Drawing Sheet

METHOD AND COMPOSITION FOR ACUTE TREATMENT OF SEIZURES

RELATED APPLICATIONS

This application claims priority of U.S. Provisional Application No. 62/397,666, filed on Sep. 21, 2016, and U.S. Provisional Application No. 62/502,884 filed on May 8, 2017, the contents of each of which are hereby incorporated by reference as if fully set forth herein.

FIELD OF INVENTION

The present disclosure generally relates to a nasal spray for treating ailments, and a method of using the same. In embodiments, the nasal spray may be used to treat seizures. In embodiments the nasal spray may be used to treat self-injurious behavior associated with autism.

BACKGROUND OF THE INVENTION

Throughout this application various publications are referred to. Full citations for the references may be found at the end of the specification. The disclosures of these publications are hereby incorporated by reference in their entirety into the subject application to more fully describe the art to which the subject disclosure pertains.

The current standard procedure for treating a patient with epilepsy undergoing a convulsive seizure is administration of benzodiazepines, usually by intravenous or intramuscular delivery. Phenytoin may be administered if a second drug is needed. (See, e.g., Tyson Pillow et al.) Both of these drugs have known undesirable side-effects.

Autism spectrum disorder (ASD) manifest itself in a wide array of symptoms. Some subjects with ASD experience physical self-injurious behavior, which is harmful to the subject—such as head-banging, hand-biting, excessive scratching, and is distressing to caregivers (see Edelson, Autism Research Institute)

In embodiments, the present disclosure addresses the need for a new method and product for treating and ameliorating seizures, including epileptic seizures, during their occurrence.

In embodiments, the present disclosure addresses the need for a new method and product for treating and ameliorating self-injurious behavior, in subjects with ASD, during its occurrence.

SUMMARY OF THE INVENTION

The present disclosure generally relates to a nasal spray for treating ailments, and a method of using the same. In embodiments, the nasal spray may be used to treat seizures. In embodiments the nasal spray may be used to treat self-injurious behavior associated with autism.

In embodiments, a method is provided of reducing the severity of a seizure in a human subject, wherein the human subject is undergoing a seizure, comprising intranasally administering to the subject an amount of a composition comprising a delta-9-tetrahydrocannabinol and one or more terpenes effective to reduce the severity of a seizure in a human subject.

Also provided in embodiments is a method of reducing the severity of a self-injurious behavior in an autistic human subject, wherein the human subject is undergoing a self-injurious behavior comprising intranasally administering to the subject an amount of a composition comprising a delta-9-tetrahydrocannabinol and one or more terpenes effective to reduce the severity of a self-injurious behavior in an autistic human subject.

A nasal spray composition is provided for application in a nostril of a human comprising: (a) 5% by volume delta-9-tetrahydrocannabinol; (b) one or more terpenes, wherein the nasal spray composition is applied in a first dose of approximately 0.1 ml spray comprising 5 mg of delta-9-tetrahydrocannabinol over a first period of less than 5 seconds to the nostril.

Additional objects of the disclosure will be apparent from the description which follows.

BRIEF DESCRIPTION OF THE DRAWINGS

Exemplary embodiments of the present disclosure will be described with references to the accompanying figures, wherein:

FIG. 1: Illustrates a front view of a nasal spray bottle for delivery of nasal spray in accordance with an exemplary embodiment of the present disclosure.

DETAILED DESCRIPTION OF THE INVENTION

The present disclosure generally relates to a nasal spray for treating ailment, and a method of using the same. In embodiments, the nasal spray may be used to treat seizures, such as convulsive seizures. In embodiments the nasal spray may be used to treat self-injurious behavior associated with autism.

A nasal spray in accordance with exemplary embodiments of the present disclosure may be comprised of a delta-9-tetrahydrocannabinol and one or more terpenes. The spray may be administered intranasally as droplets in a spray form using a nasal spray bottle such as shown in FIG. 1. In embodiments, the nasal spray bottle may be child resistant and/or tamper proof. In embodiments, the nasal spray may be administered using an aerosol bottle employing physiologically acceptable or pharmaceutically acceptable propellant(s). In embodiments, the aerosol bottle may be child resistant and/or tamper proof.

In embodiments, the dosage of approximately 0.1 ml administered may comprise 2.5 mg to 5.0 mg, or 5 mg or 10 mg, or 10 mg to 20 mg of delta-9-tetrahydrocannabinol and 2% to 14% by volume, or 4% to 12% by volume or 6% to 10% by volume; or 8% by volume of linalool (3,7-Dimethylocta-1,6-dien-3-ol) or other terpenes such as limonene, myrcene, α-pinene, β-caryophyllene, caryophyllene oxide, nerolidol, and phytol. In embodiments, the dosage of approximately 0.1 ml administered may comprise 2.5, 4.5, 5, 10 or 20% by volume of delta-9-tetrahydrocannabinol and 2% to 14% by volume, or 4% to 12% by volume or 6% to 10% by volume; or 8% by volume of linalool (3,7-Dimethylocta-1,6-dien-3-ol) or other terpenes such as limonene, myrcene, α-pinene, β-caryophyllene, caryophyllene oxide, nerolidol, and phytol.

In embodiments, the linalool, or other terpene, is present at a level in the composition which is enriched relative to the level of linalool, or other terpene, that can be found in a *C. sativa* plant of the cannabaceae family. It is understood that linalool is not present at a level of 8% in *C. sativa*. In an embodiment, the linalool in the composition contains linalool derived or extracted from *C. sativa* and linalool derived from one or more of Lamiaceae, Lauraceae, Birch Tree and Citrus. In an embodiment, the linalool, or other terpene, is derived from non-GMO source(s). In an embodiment, the linalool, or other terpene, is not derived from non-GMO source(s). As used herein, a GMO source is a source that contains, or that is parented by an organism that contains, genetic material that has been altered in a way that does not occur naturally by mating and/or natural recombination. In embodiments, the composition comprises one or more other terpenes. In embodiments, the one or more other terpenes are selected from limonene, myrcene, α-pinene, β-caryophyllene, caryophyllene oxide, nerolidol, and phytol.

In embodiments, the composition further comprises one or more of cannabidiol (CBD), cannabigerol (CBG), cannabinol (CBN), cannabichromene (CBC), and tetrahydrocannabivarin (THCV).

In embodiments, a first dosage of the nasal spray may be administered intranasally while a subject (such as one with epilepsy) is undergoing a seizure (such as a convulsive seizure) to reduce the severity of such seizure. In embodiments, a second dosage of the nasal spray may be administered intranasally if the seizure persists.

In embodiments, a first dosage of the nasal spray may be administered intranasally while a subject (such as one with autism) is undergoing a self-injurious behavior (such as self-hitting) to reduce the severity of such behavior. In embodiments, a second dosage of the nasal spray may be administered intranasally if the self-injurious behavior persists. In embodiments, the self-injurious behavior is self-hitting or self-biting.

The disclosure disclosed herein does not require heating of the active ingredient(s), or combustion of materials containing the active ingredient(s), to work. In embodiments, the active ingredient(s) or composition comprising such are administered at room temperature or ambient temperature.

A method is provided of reducing the severity of a seizure in a human subject, wherein the human subject is undergoing a seizure, comprising intranasally administering to the subject an amount of a composition comprising a delta-9-tetrahydrocannabinol and one or more terpenes effective to reduce the severity of a seizure in a human subject.

In embodiments, the seizure is a convulsive seizure and the administration effects cessation of convulsions of the seizure or reduces severity of convulsion of the seizure. In embodiments, the convulsive seizure is a grand-mal seizure or tonic-clonic seizure.

In embodiments, the human subject has epilepsy. In embodiments, the convulsive seizure is an epileptic convulsive seizure.

In an embodiment of the methods, the pre-seizure aura experienced by a subject is not considered a state of undergoing a seizure, and is excluded from the phrase "undergoing a seizure" as used herein. In an alternative embodiment, the pre-seizure aura experienced by a subject is considered part of seizure initiation and is specifically included in the phrase "undergoing a seizure" as used herein.

A method is provided of preventing or reducing the severity of a seizure in a human subject, wherein the human subject is undergoing a pre-seizure aura, comprising intranasally administering to the subject during the aura an amount of a composition comprising a delta-9-tetrahydrocannabinol and one or more terpenes effective to prevent or reduce the severity of a seizure in a human subject. In an embodiment, the subject undergoing the aura is not yet undergoing a physical seizure. In an embodiment, the method is for reducing the severity of a seizure in a human subject.

Also provided is a method of reducing the severity of a self-injurious behavior in an autistic human subject, wherein the human subject is undergoing a self-injurious behavior comprising intranasally administering to the subject an amount of a composition comprising a delta-9-tetrahydrocannabinol and one or more terpenes effective to reduce the severity of a self-injurious behavior in an autistic human subject.

In embodiments, the self-injurious behavior is self-hitting. In embodiments, the self-injurious behavior is self-biting.

In embodiments of the methods, the amount of the composition comprising a delta-9-tetrahydrocannabinol and one or more terpenes comprises 5 mg of delta-9-tetrahydrocannabinol.

In embodiments of the methods, the amount of the composition comprising a delta-9-tetrahydrocannabinol and one or more terpenes comprises 10 mg of delta-9-tetrahydrocannabinol.

In embodiments, the subject is a human subject of 16 years or less in age.

In embodiments, the subject is a human subject over 16 years in age.

In embodiments, the composition comprises at least 4.5% by volume delta-9-tetrahydrocannabinol.

In embodiments, the amount of the composition comprising a delta-9-tetrahydrocannabinol and one or more terpenes comprises 5% by volume delta-9-tetrahydrocannabinol.

In embodiments, the amount of the composition comprising a delta-9-tetrahydrocannabinol and one or more terpenes comprises 10% by volume delta-9-tetrahydrocannabinol.

In embodiments, the composition is delivered as spray of droplets via a first nostril of the subject.

In embodiments, the amount of the composition administered is administered as a nasal spray in an amount of approximately 0.1 ml.

In embodiments, the methods further comprise administering to the subject a second dose of the amount of the composition, via the first nostril or via a second nostril of the subject. In embodiments, the second dose of the amount of the composition administered is administered as a nasal spray in an amount of approximately 0.1 ml.

In embodiments, the second dose of the amount of the composition is administered within 10 seconds of a first amount of the composition being administered. In embodiments, the second dose of the amount of the composition is administered 30 seconds or more after a first amount of the composition being administered.

In embodiments of the methods, the amount of the composition administered is administered as a nasal spray from a child-resistant applicator bottle.

In embodiments, the composition is not self-administered.

In embodiments, the amount of the composition comprising delta-9-tetrahydrocannabinol is administered to the subject within a time period of less than 2.5 seconds.

In embodiments, the amount of the composition comprising delta-9-tetrahydrocannabinol is administered to the subject within a time period of less than 2.0 seconds.

In an embodiment, the severity of a convulsion seizure is reduced within a time period of less than 15 minutes from administration of the amount of the composition. In an embodiment, the severity of a convulsion seizure is reduced within a time period of less than 5 minutes from administration of the amount of the composition. In an embodiment, the severity of a convulsion seizure is reduced within a time period of less than 1 minute from administration of the amount of the composition. In an embodiment, the severity of a convulsion seizure is reduced within a time period of less than 20 seconds from administration of the amount of the composition. In an embodiment, the severity of a convulsion seizure is reduced within a time period of less than 15 seconds from administration of the amount of the composition.

In an embodiment, the severity of the seizure is reduced within a time period of less than 15 minutes from administration of the amount of the composition. In an embodiment, the severity of the seizure is reduced within a time period of less than 5 minutes from administration of the amount of the composition. In an embodiment, the severity of the seizure is reduced within a time period of less than 1 minute from administration of the amount of the composition. In an embodiment, the severity of the seizure is reduced within a time period of less than 20 seconds from administration of the amount of the composition.

In an embodiment, the severity of the self-injurious behavior is reduced within a time period of less than 15 minutes from administration of the amount of the composition. In an embodiment, the severity of the self-injurious behavior is reduced within a time period of less than 5 minutes from administration of the amount of the composition. In an embodiment, the severity of the self-injurious behavior is reduced within a time period of less than 1 minute from administration of the amount of the composition. In an embodiment, the severity of the self-injurious behavior is reduced within a time period of less than 20 seconds from administration of the amount of the composition.

In embodiments, the severity of a convulsion seizure is reduced within a time period of less than 20 seconds from administration of the amount of the composition.

In embodiments, the severity of a convulsion seizure is reduced within a time period of less than 15 seconds from administration of the amount of the composition.

In embodiments, the severity of the seizure is reduced within a time period of less than 20 seconds from administration of the amount of the composition.

In an embodiment, the severity of the seizure is reduced in that the rate of convulsions is reduced. In an embodiment, the severity of the seizure is reduced in that the rate of convulsions per 5 or 10 seconds is reduced.

In embodiments, the severity of the self-injurious behavior is reduced within a time period of less than 20 seconds from administration of the amount of the composition.

In an embodiment, the rate of self-injurious hitting is reduced. In an embodiment, the rate of self-injurious hitting per 5 or 10 seconds is reduced relative to the rate of self-injurious hitting per 5 or 10 seconds during the self-injurious behavior before administration of the composition. In an embodiment, the rate of self-injurious biting is reduced. In an embodiment, the rate of self-biting per 5 or 10 seconds is reduced relative to the rate of self-biting per 5 or 10 seconds during the self-injurious behavior before administration of the composition.

In a further embodiment for treating seizures, the onset of the therapeutic response is 20-120 seconds following administration of the spray. In an embodiment, the peak therapeutic effect can be achieved later, for example at 10-30 minutes after administration.

In a further embodiment for treating self-injury in autism, the onset of the therapeutic response is present by 2-15 minutes. In an embodiment, the peak therapeutic effect can be achieved later, for example at 10-30 minutes after administration.

In embodiments, the one or more terpenes comprise linalool (3,7-Dimethylocta-1,6-dien-3-ol).

In embodiments, the one or more terpenes comprise linalool (3,7-Dimethylocta-1,6-dien-3-ol) at up to 9% by volume.

In embodiments, the one or more terpenes comprise linalool (3,7-Dimethylocta-1,6-dien-3-ol) at 8% by volume.

In embodiments, the one or more terpenes are plant-derived.

In embodiments, the composition further comprises one or more of CBD, CBG, CBN, CBC, and THCV.

In embodiments, the composition comprises medium chain triglycerides.

In embodiments, the medium chain triglycerides are coconut derived.

In embodiments, the delta-9-tetrahydrocannabinol in the composition is substantially (−)-trans-$\Delta^9$-tetrahydrocannabinol.

In embodiments of the methods herein, the methods further comprise positioning the subject's head downwards and in a forward position prior to intranasally administering the composition.

In embodiments, the intranasal administration effects delivery to the olfactory epithelium of the subject. As is known in the art, the olfactory epithelium is a specialized epithelial tissue inside the nasal cavity that is involved in smell. In humans, it measures about 9 $cm^2$ and is positioned on the roof of the nasal cavity above and behind the nostrils.

In embodiments, the intranasal administration is delivered as a spray of liquid droplets.

In embodiments of the methods herein, the amount of the composition is administered at room temperature. In embodiments of the methods herein, the amount of the composition is administered at a composition temperature of 15° C. (59° F.) and 25° C. (77° F.). In embodiments of the methods herein, the amount of the composition is administered at a composition temperature below 15° C. (59° F.). In embodiments of the methods herein, the amount of the composition is not heated above ambient temperature. In embodiments of the methods herein, the amount of the composition is not vaporized using a heat source. In embodiments of the methods herein, the amount of the composition is not vaporized using an electrical source. In embodiments of the methods herein, the amount of the composition is not combusted.

A nasal spray composition is provided for application in a nostril of a human comprising: (a) 5% by volume delta-9-tetrahydrocannabinol, (b) one or more terpenes, wherein the nasal spray composition is applied in a first dose of approximately 0.1 ml spray comprising 5 mg of delta-9-tetrahydrocannabinol over a first period of less than 5 seconds to the nostril.

In embodiments, the nasal spray composition is further applied in a second dose of approximately 0.1 ml spray comprising 5 mg delta-9-tetrahydrocannabinol over a second period of less than 5 seconds within 20 seconds to a different nostril of the same human.

In embodiments, the one or more terpenes comprise linalool (3,7-Dimethylocta-1,6-dien-3-ol).

In embodiments, the nasal spray is stored in a nasal spray bottle for use with application, wherein the nasal spray bottle comprises a tamper-proof child resistant container that dispenses the nasal spray in 0.1 ml units.

In embodiments, the first dose of the nasal spray is applied in the nostril of the human while the human is having a convulsive seizure.

In embodiments, the first dose of the nasal spray is applied in the nostril of the human while the human is having a non-epileptic seizure.

In embodiments, the first dose of the nasal spray is applied in the nostril of the human while the human is having an epileptic seizure.

In embodiments, the first dose of the nasal spray is applied in the nostril of the human while the human is having a convulsive seizure and a second dose is applied to the other nostril of the human while the convulsive seizure continues.

In embodiments, the first dose of the nasal spray is applied to the nostril of the human while the human is having a self-injurious behavior associated with autism.

In embodiments, the volume of the nasal spray is 1 fluid ounce.

In embodiments, the nasal spray contains three hundred 5 mg doses of the delta-9-tetrahydrocannabinol and one or more terpenes.

In embodiments, the nasal spray is delivered as a spray of liquid droplets. In an embodiment, the nasal spray composition is provided in a bottle comprising an atomizer.

In embodiments, the delta-9-tetrahydrocannabinol in the composition is substantially (−)-trans-$\Delta^9$-tetrahydrocannabinol.

In embodiments, the composition further comprises one or more of cannabidiol (CBD), cannabigerol (CBG), cannabinol (CBN), cannabichromene (CBC), and tetrahydrocannabivarin (THCV).

In embodiments, the composition comprises medium chain triglycerides (MCT). In embodiments, the MCT are coconut derived.

In embodiments, the composition comprises one or more additional terpenes.

In embodiments, the composition further comprises one or more terpenoids.

In embodiments, the nasal spray composition is provided in a bottle with a tamper-evident seal. In embodiments, the nasal spray composition is provided in a bottle with a child resistant lid. In embodiments, the nasal spray composition is provided in a bottle with a manual atomizer pump.

In embodiments of the methods or compositions, delta-9-tetrahydrocannabinol is present at 2.5% or greater by volume in the composition. In an embodiment, delta-9-tetrahydrocannabinol is present at 2.5% by volume in the composition. In an embodiment, delta-9-tetrahydrocannabinol is present at 5% or greater by volume in the composition. In an embodiment, delta-9-tetrahydrocannabinol is present at 5% by volume in the composition. In an embodiment, delta-9-tetrahydrocannabinol is present at 10% or greater by volume in the composition. In an embodiment, delta-9-tetrahydrocannabinol is present at 10% by volume in the composition.

In embodiments, the MCT are present at 4.5-5.0% by volume in the composition. In embodiments, the MCT are present at 5.0% by volume in the composition. In embodiments, the MCT are present at 4.5-5.0% by volume in the composition.

In embodiments, the MCT are present at 80% or more by volume in the composition.

In embodiments, the one or more terpenes comprise linalool (3,7-Dimethylocta-1,6-dien-3-ol).

The method can be applied, mutatis mutandis, to veterinary subjects with epilepsy undergoing a convulsive seizure in order to effect cessation of the convulsions of the seizure. For example, canine subjects with epilepsy undergoing a convulsive seizure.

In an embodiment the convulsive seizure is a grand-mal seizure or tonic-clonic seizure. In adult dogs, at least one, and up to four, 0.1 ml doses (each dose 5 mg delta-9-tetrahydrocannabinol with 8% by volume linalool) are administered during a convulsive seizure in order to effect cessation of the seizure convulsions.

In embodiments, "approximately" as used herein with regard to a stated amount, means within a range encompassing from 10% below to 10% above the stated amount. In a different embodiment, the disclosure also provides all amounts otherwise herein indicated as approximately, to be the amounts exactly expressed as the stated amount.

All ranges disclosed herein are to be understood to encompass any and all subranges subsumed therein. For example, a stated range of "1 to 10" should be considered to include any and all subranges between (and inclusive of) the minimum value of 1 and the maximum value of 10; that is, all subranges beginning with a minimum value of 1 or more and ending with a maximum value of 10 or less, e.g., 1 to 6.3, or 5.5 to 10, or 2.7 to 6.1.

All combinations of the various elements described herein are within the scope of the disclosure unless otherwise indicated herein or otherwise clearly contradicted by context.

This invention will be better understood from the Examples which follow. However, one skilled in the art will readily appreciate that the specific methods and results discussed are merely illustrative of the invention as described more fully in the claims that follow thereafter.

EXAMPLE 1

Three male human pediatric subjects, each under the age of 16, undergoing convulsive seizures, were administered from two to four 0.1 ml doses (each dose 5 mg delta-9-tetrahydrocannabinol with 8% by volume linalool) of the product disclosed herein. Administration was achieved via a nasal spray administered within one or more of the subject's nostrils using the delivery device disclosed herein by a caregiver during the occurrence of the convulsive seizure. In subject one, administered 3 doses, a visible state of cessation of the convulsions of the seizure was achieved by 21 seconds from first dose administration. In subject two, administered 4 doses, a visible state of cessation of the convulsions of the seizure was achieved by 36 seconds from first dose administration. In subject three, administered 2 doses, a visible state of cessation of the convulsions of the seizure was achieved by 27 seconds from first dose administration.

Thus, acute treatment of the convulsive seizure using an average dose of 3×0.1 ml of the 5 mg delta-9-tetrahydrocannabinol with 8% by volume linalool achieved cessation of the convulsion symptom of the convulsive seizure within a mean time of 28 seconds from first dose administration.

EXAMPLE 2

In adults, a stronger dose is administered, preferably at least one, and up to four, 0.1 ml doses of 10 mg delta-9-tetrahydrocannabinol with 8% by volume linalool. Cessation of the convulsion symptom of the convulsive seizure is effected soon after first dose administration.

EXAMPLE 3

A 15-year old male subject with a diagnosis of epilepsy and severe autism was treated. It was reported by the caregiver that oftentimes preceding his epileptic seizures, the subject is agitated and inflicts self-injurious behavior. During one of these self-injurious behavior events up to four 0.1 ml doses (each dose 5 mg delta-9-tetrahydrocannabinol with 8% by volume linalool) of a composition disclosed herein were administered via a nasal spray within the subject's nostrils using the delivery device disclosed herein by the caregiver. Cessation of the self-injurious behavior occurred shortly after administration. Thereafter, unlike prior incidents of self-injurious behavior there was no subsequent epileptic event detected as would have been otherwise expected. The caregiver reported no observable adverse effects with this approach.

In accordance with exemplary embodiments of the present invention, in the case of an older teenager or adult with autism, when undergoing a self-injurious behavior event, a strong dose can be administered, preferably at least one, and up to four, 0.1 ml doses (each dose 10 mg delta-9-tetrahydrocannabinol with 8% by volume linalool). Also, in accordance with exemplary embodiments of the present invention, a younger pediatric subject, e.g. 10 years, with autism undergoing a self-injurious behavior event can be given at least one, and up to four, 0.1 ml doses (each dose 5 mg delta-9-tetrahydrocannabinol with 8% by volume linalool) via a nasal spray administered within one or more of the subject's nostrils using the delivery device disclosed herein by a caregiver during the occurrence of the self-injurious behavior event.

Discussion

Disclosed herein is a very effective method and product for treating convulsive symptoms of a convulsive seizure, such as exhibited in epilepsy. The prior art (see Wallace et al., 2003) discloses administering high doses of THC (30.0 mg/kg) by intraperitoneal injection into a rat model of epilepsy can prevent seizures from occurring, but that THC only starts to have an anticonvulsant effect at doses of 5.0 mg/kg, with an ED50 of 15.0 mg/kg. Notably, in contrast to the present disclosure, Wallace et al. does not administer the THC acutely during a seizure to treat the seizure, rather what Wallace et al. discloses is seizure prevention with THC. The present disclosure is unexpectedly superior, with seizures in progress being treated and stopped in human subjects at doses as low as 10.0 mg total THC administered dose for subjects weighing over 60 lbs (i.e. around 0.37 mg/kg). This is starkly different, and not predictable from, the disclosure in Wallace et al. of the 15 mg/kg ED50 for seizure prevention, and is a treatment effect at a dose around 13.5 times lower than 5.0 mg/kg dose disclosed in the art to be the minimum starting dose for anticonvulsant effect in the prior art. Wallace et al. also teaches away from using THC itself for epilepsy by stating that cannabinoids are psychoactive making "their use in the treatment of epilepsy impractical" and further indicating "novel compounds" should be developed instead.

Moreover, while there was still debate in the art prior to filing as to whether therapeutic amounts of a drug can be delivered via the human olfactory epithelium (e.g. see Illum), the results presented herein demonstrate efficacy in treating convulsive seizure activity through nasally administered delta-9-tetrahydrocannabinol. The results presented herein also demonstrate efficacy in treating self-injurious activity in autism through nasally administered delta-9-tetrahydrocannabinol.

In this regard, without wishing to be bound by theory, it is understood that the delta-9-tetrahydrocannabinol may be acting via the olfactory epithelia of the subject. This effect may be enhanced by an entourage effect of the co-administered terpene(s) (e.g. linalool) and/or other cannabinoids and/or terpenoids and/or flavonoids (see, e.g., Russo et al., *British Journal of Pharmacology* (2011) 163 1344-1364, hereby incorporated by reference). In this regard, the correct head position may facilitate absorption into the brain (Mittal et al., 2011). For example, during intranasal delivery, drainage of the formulation into the esophagus and trachea can reduce the concentration measured in the cerebral spinal fluid. An ideal position for brain targeting of nasally administered formulations is with head down and forward position (Mittal et al., (2014), Insights into direct nose to brain delivery: current status and future perspective, Drug Delivery, 21:2, 75-86, DOI: 10.3109/10717544.2013.83871, hereby incorporated by reference). However, given the rapidity of the response observed visually in the test subjects, independent or additional mechanism(s) may be in play.

REFERENCES

1. Edelson, S. M., "Understanding and Treating Self-Injurious Behavior" on the world wide web at autism.com/symptoms_self-injury
2. L. Illum. Is nose-to-brain transport of drugs in man a reality? *J Pharm Pharmacol.* 56:3-17 (2004).
3. Tyson Pillow, "Seizure Assessment in the Emergency Department", accessible on MedScape on the world wide web at emedicine.medscape.com/article/1609294-overview#a11.
4. Wallace et al., *J. Pharm. Exp. Ther.*, (2003), 307(1):129-137.

What is claimed is:

1. A method for reducing severity of an epileptic seizure, the method comprising:
   providing a composition that includes delta-9-tetrahydrocannabinol and one or more terpenes; and
   intranasally administering the composition to a human subject while the human subject is actively convulsing from the epileptic seizure, the human subject incapable of administering the composition while actively convulsing.

2. A method for reducing severity from an epileptic seizure, the method comprising:
   providing a composition that includes one or more terpenes and between 5% and 10% of delta-9-tetrahydrocannabinol by volume; and
   intranasally administering approximately 0.1 ml of the composition to a human subject while the human subject is actively convulsing from a seizure consisting only of the epileptic seizure, the human subject incapable of administering the composition while actively convulsing.

* * * * *